(12) United States Patent
Jeoung et al.

(10) Patent No.: US 10,239,924 B2
(45) Date of Patent: *Mar. 26, 2019

(54) PEPTIDE HAVING EIGHT AMINO ACID SEQUENCES DERIVED FROM CAGE AND RETAINING ANTICANCER ACTIVITY AND ACTIVITY TO PROMOTE ANTICANCER DRUG SENSITIVITY OF ANTICANCER DRUG-RESISTANT CANCER CELLS

(71) Applicant: L-Base Co., Ltd., Seoul (KR)

(72) Inventors: Doo Il Jeoung, Seoul (KR); Young Mi Kim, Chuncheon-si (KR); Hyun A Kim, Chuncheon-si (KR)

(73) Assignee: L-BASE CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/624,906

(22) Filed: Jun. 16, 2017

(65) Prior Publication Data

US 2018/0057532 A1 Mar. 1, 2018

Related U.S. Application Data

(63) Continuation of application No. PCT/KR2015/013920, filed on Dec. 18, 2015.

(30) Foreign Application Priority Data

Dec. 18, 2014 (KR) .......................... 10-2014-0183218

(51) Int. Cl.
| | |
|---|---|
| *A61K 38/08* | (2006.01) |
| *A61K 38/06* | (2006.01) |
| *A61K 45/06* | (2006.01) |
| *C07K 7/06* | (2006.01) |
| *C07K 7/00* | (2006.01) |
| *C07K 14/47* | (2006.01) |
| *A61K 31/192* | (2006.01) |
| *A61K 31/337* | (2006.01) |
| *A61K 38/00* | (2006.01) |

(52) U.S. Cl.
CPC ........ *C07K 14/4748* (2013.01); *A61K 31/192* (2013.01); *A61K 31/337* (2013.01); *A61K 38/08* (2013.01); *A61K 45/06* (2013.01); *C07K 7/06* (2013.01); *A61K 38/00* (2013.01)

(58) Field of Classification Search
CPC .......... A61K 38/08; A61K 45/06; C07K 7/06; C07K 7/00; C07K 14/4748; C07K 14/47
USPC ................. 530/300, 328; 514/1.1, 19.2, 21.7
See application file for complete search history.

(56) References Cited

U.S. PATENT DOCUMENTS

2013/0330335 A1* 12/2013 Bremel .................. G06F 19/18
424/134.1

OTHER PUBLICATIONS

Robert G. Maki et al., Human homologue of murine tumor rejection antigen gp96: 5'-Regulatory and coding regions and relationship to stress-induced proteins, Proc. Natl. Acad. Sci. USA, vol. 87, p. 5658-5662, Aug. 1990.
Matteo Bellone et al., Cancer immunotherapy: synthetic and natural peptides in the balance, Viewpoint Immunology Today, vol. 20, No. 10, p. 457-462, Oct. 1999.
Bomsoo Cho et al., Identification and Characterization of a Novel Cancer/Testis Antigen Gene CAGE, Biochemical and Biophysical Research Communications 292, p. 715-726, Mar. 2002.
Bomsoo Cho et al., Promoter hypomethylation of a novel cancer/testis antigen gene CAGE is correlated with its aberrant expression and is seen in premalignant stage of gastric carcinoma, Biochemical and Biophysical Research Communications 307, p. 52-63, May 2003.
Youngmi Kim et al., The cancer/testis antigen CAGE induces MMP-2 through the activation of NF-kB and AP-1, BMB Rep. Nov. 30, 2009, 42(11): p. 758-763.
Eunsook Shim et al., CAGE displays oncogenic potential and induces cytolytic T lymphocyte activity, Biotechnology Letters, Jan. 10, 2006, vol. 28, p. 515-522.

* cited by examiner

*Primary Examiner* — Julie Ha
(74) *Attorney, Agent, or Firm* — Lucas & Mercanti, LLP

(57) ABSTRACT

A peptide having eight amino acid sequences derived from cancer-associated gene (CAGE) is described which retains anticancer activity and activity to promote anticancer drug sensitivity of anticancer drug resistant cancer cells. Specifically, a peptide which has an amino acid sequence of SEQ ID NO: 1 (AQTGTGKT) and thus binds to the CAGE protein is disclosed, which inhibits an inter-linkage between CAGE and GSK3β, thus exhibiting anticancer activity and activity to promote anticancer drug sensitivity of anticancer drug resistant cancer cells. A pharmaceutical composition is also disclosed containing the peptide with the amino acid sequence of SEQ ID NO: 1 (AQTGTGKT), for anticancer use or anticancer drug aiding.

9 Claims, 11 Drawing Sheets

Specification includes a Sequence Listing.

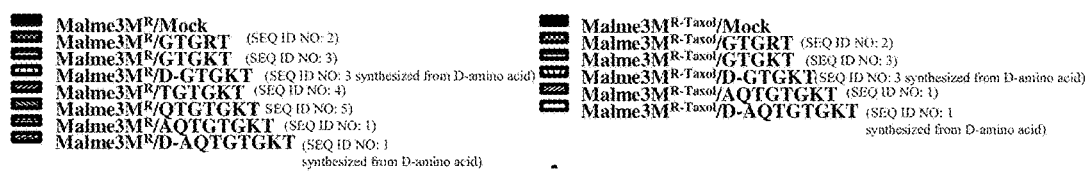
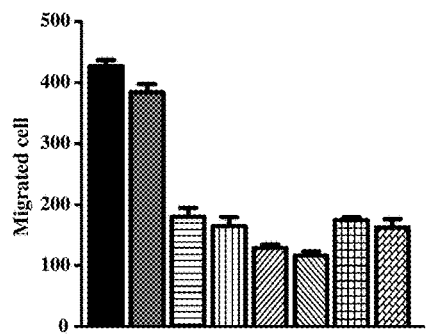
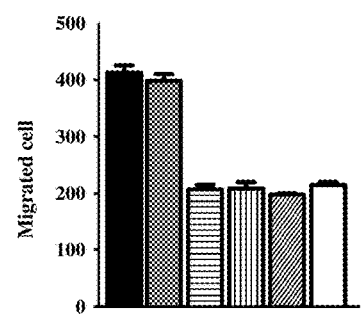
FIG. 5A1    FIG. 5A2

```
SEQUENCE LISTING

<160> NUMBER OF SEQ ID NOS: 6

<210> SEQ ID NO 1
<211> LENGTH: 8
<212> TYPE: PRT
<213> ORGANISM: Homo sapiens

<400> SEQUENCE: 1

Ala Gln Thr Gly Thr Gly Lys Thr
1               5

<210> SEQ ID NO 2
<211> LENGTH: 5
<212> TYPE: PRT
<213> ORGANISM: Artificial Sequence
<220> FEATURE:
<223> OTHER INFORMATION: truncated variant

<400> SEQUENCE: 2

Gly Thr Gly Arg Thr
1               5

<210> SEQ ID NO 3
<211> LENGTH: 5
<212> TYPE: PRT
<213> ORGANISM: Artificial Sequence
<220> FEATURE:
<223> OTHER INFORMATION: truncated variant

<400> SEQUENCE: 3

Gly Thr Gly Lys Thr
1               5

<210> SEQ ID NO 4
<211> LENGTH: 6
<212> TYPE: PRT
<213> ORGANISM: Artificial Sequence
<220> FEATURE:
<223> OTHER INFORMATION: truncated variant

<400> SEQUENCE: 4

Thr Gly Thr Gly Lys Thr
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: truncated variant

<400> SEQUENCE: 5

Gln Thr Gly Thr Gly Lys Thr
1               5

<210> SEQ ID NO 6
<211> LENGTH: 4
<212> TYPE: PRT
<213> ORGANISM: Artificial Sequence
<220> FEATURE:
<223> OTHER INFORMATION: truncated variant

<400> SEQUENCE: 6

Gly Thr Gly Lys
1
```

PEPTIDE HAVING EIGHT AMINO ACID SEQUENCES DERIVED FROM CAGE AND RETAINING ANTICANCER ACTIVITY AND ACTIVITY TO PROMOTE ANTICANCER DRUG SENSITIVITY OF ANTICANCER DRUG-RESISTANT CANCER CELLS

BACKGROUND OF THE INVENTION

Field of the Invention

The present invention relates to a peptide having a sequence of eight amino acids derived from CAGE (cancer-associated antigen gene) and retaining anticancer activity and activity to promote anticancer drug sensitivity of anticancer drug-resistant cancer cells and, specifically, to a peptide which exhibits anticancer activity and activity to promote anticancer drug sensitivity of anticancer drug-resistant cancer cells by having the amino acid sequence of SEQ ID NO: 1 (AQTGTGKT) and thus binding to CAGE protein to inhibit the interconnection of CAGE and GSK3β, to a pharmaceutical composition containing the peptide for anticancer use or anticancer drug aid.

Discussion of the Related Art

Cancer is still an important disease in the first or second place among the causes of death in Korea in spite of the improvement of cancer treatment due to the development of early diagnosis of cancer and the continuous development of new cancer therapy. Most of the currently used anticancer drugs are by chemotherapy, which is indicated as a problem of cancer treatment because the drugs have various pharmacological action and various toxicity-causing side effects according to the type of cancer. Conventional anticancer drugs invade not only cancer cells but also normal tissues to damage functions and activity of normal cells, showing great problems in cancer treatment, for example, causing side effects, such as bone marrow dysfunction, gastrointestinal disorder, and alopecia, or exhibiting multi-drug resistance to anticancer drugs due to long-term chemotherapy. Therefore, the development of innovative anticancer drugs capable of solving such serious problems of existing anticancer drugs is being actively studied.

After it was first reported that cancer patients can cause immune responses to their antigens in the 1990s (Lloyd et al., 1990, Proc. Natl. Acad. Sci., 87, 5658-5662), several genes encoding tumor antigens were isolated using tumor-specific cytotoxic T lymphocytes (CTLs) (Van den Eynde, B. J. et al., 1997, Curr. Opin. Immunol., 9, 684-693). In addition, autologous antigens existing in cancer patients were found using the serum of cancer patients through a reaction with recombinant cDNA expression libraries prepared from various cancer tissues, and these autologous antigens are named tumor associated antigens (TAAs). Of these, cancer/testis antigens including melanoma associated antigen (MAGE), GAGE, and BAGE are antigens encoded by the genes that are expressed in various tumors originated from different tissues but not expressed in normal tissues other excluding testicular germ cells.

Cancer/testis antigens are currently the subject of the development of cancer diagnostic marker proteins and anticancer vaccines. For example, it has been reported that six out of tumor antigens of the MAGE family, that is, MAGE-1, 2, 3, 4, 6 and 12 are selectively expressed by a considerable portion of primary tumors and metastatic tumors, including melanoma, lung cancer, bladder cancer, ovarian cancer, and breast cancer.

The cancer/testis antigen cancer associated gene (CAGE) has been found as a novel cancer/testis antigen that is specifically present in the serum of the gastric cancer patients using serologic analysis of recombinant cDNA library expression (SEREX) from cDNA expression libraries prepared in gastric cancer cell lines and testis tissues (Cho B., 2002, Biochem. Biophys. Res. Commun., 295, 715-726). In addition, the relationship between the degree of DNA demethylation of CAGE gene promoter CpG island and the expression of CAGE has been established through the demethylation of the CAGE gene (Cho B., 2003, Biochem. Biophys. Res. Commun., 307, 52-63). These findings suggest the possibility of development of a new cancer diagnosis method through the analysis of methylation patterns of CAGE gene.

It was shown that: the overexpression of the CAGE gene increases cell migration and the phosphorylation of ERK, p38 MAPK, and FAK increases cell migration by CAGE (Shim H., 2006, Mol Cells, 21, 367-375); CAGE induces the expression of c-Flice inhibitory protein (cFlIP) and snail to increase cell migration and anticancer drug resistance in Celastrol-based resistant rat melanoma cell line (Kim Y., 2009, Biotechnol Lett., 31, 945-952); CAGE induces the expression of MMP-2 through the activity of NF-kB/AP-1 (Kim Y., 2009, BMB reports, 42, 758-763); CAGE inhibits the expression of p53 by an interaction with HDAC2 to give anticancer drug resistance in a Celastrol-based anticancer drug-resistant cell line (liver cancer SNU387$^R$, melanoma Malm3M$^R$), (Kim Y., 2010, J. Biol. Chem., 285, 25957-25968); and the peptides derived from the CAGE protein exhibits anticancer activity by increasing the activity of cytotoxic T lymphocytes (Shim, E., 2006, Biotechnol. Lett. 28, 515522).

Meanwhile, the present inventors have previously established through a patent application that CAGE induces anticancer drug resistance due to the phosphorylation of glycogen synthase kinase-3 β (GSK3β) ser9 residue and, resultantly, the accumulation of Cyclin D1 in the nucleus (Korean Patent Publication No. 10-2013-0030080).

Antibodies targeting tumor cell-specific tumor antigens have been developed, but such antibodies have problems, such as concerns of immune response and low efficiency in the invasion into tissues. On the other hand, it is considered that peptides have a small molecular weight, and thus, have few concerns of immune responses and are easy to invade tissues, unlike antibodies, and peptide-based anticancer drugs targeting tumor antigens can selectively act on tumors, and thus have few side effects, such as damaging normal cells.

The present inventors have reported through several conventional studies that CAGE gives resistance to anticancer drugs, as a new cancerogen, and under this background, studies on novel anti-cancer peptides targeting cancer/testis antigens CAGE was conducted. As a result, it was confirmed that the AQTGTGKT (266-273) (SEQ ID NO: 1)-based oligopeptide corresponding to an ATP binding region of the CAGE protein inhibits tumorigenicity and anticancer drug resistance of CAGE in the anticancer drug resistant cell lines, and thus, the present invention has been completed.

PRIOR ART DOCUMENTS

Patent Documents (Patent Document 0001) Korean Patent Publication No. 10-2013-0030080

Non-Patent Documents (Non-Patent Document 0001) Cho B., 2002, Biochem. Biophys. Res. Commun., 295, 715-726
(Non-Patent Document 0002) Cho B., 2003, Biochem. Biophys. Res. Commun., 307, 52-63
(Non-Patent Document 0003) Shim H., 2006, Mol Cells, 21, 367-375
(Non-Patent Document 0004) Kim Y., 2009, Biotechnol Lett., 31, 945-952
(Non-Patent Document 0005) Kim Y., 2009, BMB reports, 42, 758-763
(Non-Patent Document 0006) Kim Y., 2010, J. Biol. Chem., 285, 25957-25968
(Non-Patent Document 0007) Shim, E., 2006, Biotechnol. Lett. 28, 515522

SUMMARY OF THE INVENTION

The present invention has been invented to improve such problems, and an aspect of the present invention is to provide a novel anticancer drug having excellent anticancer activity.

Furthermore, an object of the present invention is to provide an anticancer therapy adjuvant capable of increasing a therapeutic effect of an anticancer drug by increasing the anticancer drug sensitivity of anticancer drug-resistant cancer cells.

In accordance with an aspect of the present invention, the present invention provides an isolated peptide having the amino acid sequence of SEQ ID NO: 1 (AQTGTGKT) and retaining anticancer activity and activity to promote anticancer drug sensitivity of anticancer drug-resistant cancer cells.

The peptide of the present invention may be synthesized from L-amino acid or D-amino acid.

In accordance with another aspect of the present invention, the present invention provides a pharmaceutical composition for anticancer use containing the peptide.

The pharmaceutical composition for anticancer use of the present invention is preferably used in the prevention or treatment of liver cancer or melanoma.

The pharmaceutical composition for anticancer use of the present invention is preferably used in the treatment of cancer caused by cancer cells having resistance to Celastrol or Taxol.

In accordance with still another aspect of the present invention, the present invention provides a pharmaceutical composition for anticancer drug aid containing the peptide.

The pharmaceutical composition for anticancer drug aid of the present invention is preferably used for aiding an anticancer drug in the prevention or treatment of liver cancer or melanoma.

The pharmaceutical composition for anticancer drug aid of the present invention is preferably used for aiding an anticancer drug in the treatment of cancer caused by cancer cells having resistance to Celastrol or Taxol.

The peptide of the present invention binds to the CAGE protein to inhibit the interconnection of CAGE and GSK3β, thereby inhibiting multi-drug resistance of cancer cells to anticancer drugs. Cancer associated gene (CAGE) is a cancer/testis antigen, and the amino acid sequence and gene nucleotide sequence information thereof is registered as AY039237.1 on GenBank database. Glycogen synthase kinase-3 beta (GSK3β) is registered as GCID: GC03M119540 on GeneCards database.

The peptide of the present invention is a tumor-specific peptide, and the specific invasion of the peptide into tumor tissues having high CAGE expression but not normal tissues is excellent.

The peptide of the present invention can inhibit tumorigenicity by CAGE.

The peptide of the present invention may be formulated based on the formulation standard of a conventional pharmaceutical preparation or the formulation standard of a health supplementary food in the Korean Food and Drug Administration (KFDA).

The peptide of the present invention may be used per se, or may be used in the form of a pharmaceutically acceptable acid addition salt or a metal complex, for example, salts such as zinc and iron. More specifically, the acid addition salt may be hydrogen chloride, hydrogen bromide, sulfate, phosphate, maleate, acetate, citrate, benzoate, succinate, malate, ascorbate, and tartrate.

In addition, the peptide of the present invention is preferably diluted by mixing the oligopeptide with a pharmaceutically acceptable carrier according to the administration method, administration manner, and therapeutic purpose in a conventional manner, or encapsulated in a container type carrier.

When the carrier is used as a diluent, the peptide of the present invention may be prepared in a dosage form, such as a powder, granule, injection, syrup, solution, tablet, suppository, pessary, ointment, cream, or aerosol, for oral administration and parenteral administration, using at least one carrier selected from the group consisting of saline, buffer, dextrose, water, glycerol, Ringer's solution, lactose, sucrose, calcium silicate, methyl cellulose, and ethanol. However, the carrier is not limited to the above types of carriers. Here, the parenteral administration means the administration of an active ingredient via a rectal, venous, peritoneal, muscular, arterial, transdermal, or nasal route, or inhalation, other than oral administration.

The preparation may be formulated to provide rapid, sustained, or delayed release of an active ingredient after administered to a mammal by further containing a filler, an anti-coagulant, a lubricant, a humectant, a fragrance, an emulsifier, a preservative, or the like. In addition, the dose may be adjusted according to the patient's condition, route of administration, and dosage form, but is not limited thereto, and the dose may be used according to symptom within an obviously various range by a person skilled in the art. In the present invention, the peptide of the present invention can be continuously or intermittently administered in an experimentally effective amount, about 1 mg per 1 kg of body weight a day.

BRIEF DESCRIPTION OF THE DRAWINGS

FIG. 1B illustrates MTT results showing that SEQ ID NO: 1 synthesized from L-amino acid (AQTGTGKT) or SEQ ID NO: 1 synthesized from D-amino acid (D-AQTGTGKT) peptide inhibited anticancer drug resistance in SNU387$^R$ or Malme3M$^R$ cell lines.

FIG. 5A1 illustrates the results showing that SEQ ID NO: 1 synthesized from L-amino acid (AQTGTGKT) or SEQ ID NO: 1 synthesized from D-amino acid (D-AQTGTGKT) peptide reduced the migration of Malme3M$^R$ cell line.

FIG. 5A2 illustrates the results showing that SEQ ID NO: 1 synthesized from L-amino acid (AQTGTGKT) or SEQ ID NO: 1 synthesized from D-amino acid (D-AQTGTGKT) peptide reduced the migration of Taxol-resistant melanoma cell line (Malme3M$^{R-Taxol}$).

DETAILED DESCRIPTION OF THE EMBODIMENTS

According to a first embodiment of the present invention,
disclosed is an isolated peptide having the amino acid sequence of SEQ ID NO: 1 (AQTGTGKT) and retaining anticancer activity and activity to promote anticancer drug sensitivity of anticancer drug-resistant cancer cells.

The peptide may be synthesized from L-amino acid or D-amino acid.

According to a second embodiment of the present invention,
disclosed is a pharmaceutical composition for anticancer use, the composition containing the peptide of the present invention.

The pharmaceutical composition may be used for the prevention or treatment of liver cancer or melanoma.

The pharmaceutical composition may be used for the treatment of cancer caused by cancer cells having resistance to Celastrol or Taxol.

According to a third embodiment of the present invention,
disclosed is a pharmaceutical composition for anticancer drug aid, the pharmaceutical composition containing the peptide of the present invention.

The pharmaceutical composition may be used for anticancer drug aid in the prevention or treatment of liver cancer or melanoma.

The pharmaceutical composition may be used for anticancer drug aid in the treatment of cancer caused by cancer cells having resistance to Celastrol or Taxol.

Hereinafter, the present invention will be described in detail with reference to examples. These examples are merely for illustrating the present invention, and thus the scope of the present invention is not construed to be limited to these examples.

Example 1: Examination on Effect of CAGE-Derived 8-Mer Peptide on Anticancer Drug Resistance In the present example, a peptide synthesized from L-amino acid and a peptide synthesized from D-amino acid, which have the amino acid sequence of SEQ ID NO: 1, were used.

In order to examine the effects of AQTGTGKT (SEQ ID NO: 1 synthesized from L-amino acid) or D-AQTGTGKT (SEQ ID NO: 1 synthesized from D-amino acid) peptides on the anticancer drug resistance of cancer cells, MTT assay and western blotting were conducted by a known method.

Figure 1A:
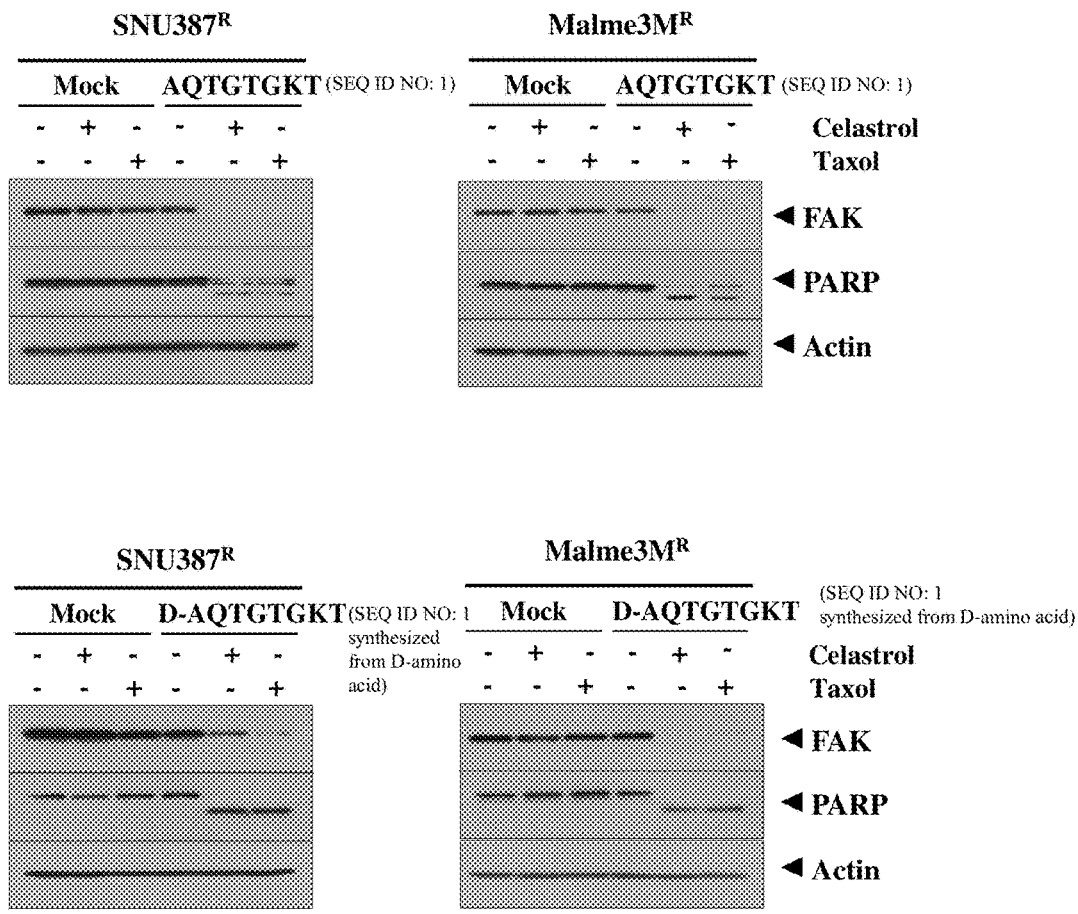
FIGS. 1A and 1B illustrate MTT results showing that AQTGTGKT (SEQ ID NO: 1 synthesized from L-amino acid) or D-AQTGTGKT peptide (SEQ ID NO: 1 peptide synthesized from D-amino acid) inhibited anticancer drug resistance in Celastrol-resistant liver cancer cell line (SNU387$^R$) or melanoma cell line (Malme3M$^R$).

Liver cancer cell line (SNU387$^R$) and melanoma cell line (Malme3M$^R$), which show resistance to Celastrol as an anticancer drug, were transfected with 1 µM AQTGTGKT (SEQ ID NO: 1 synthesized from L-amino acid) or D-AQTGTGKT (SEQ ID NO: 1 synthesized from L-amino acid) peptide for 24 hours, respectively, and then treated with 1 µM and 10 µM Celastrol and Taxol for 1 hour. The results, as shown in FIG. 1A, confirmed that the cleavage of PARP and FAK proteins, which can be frequently seen in apoptosis, was significantly observed compared with the cell lines treated without each peptide.

Figure 1B:
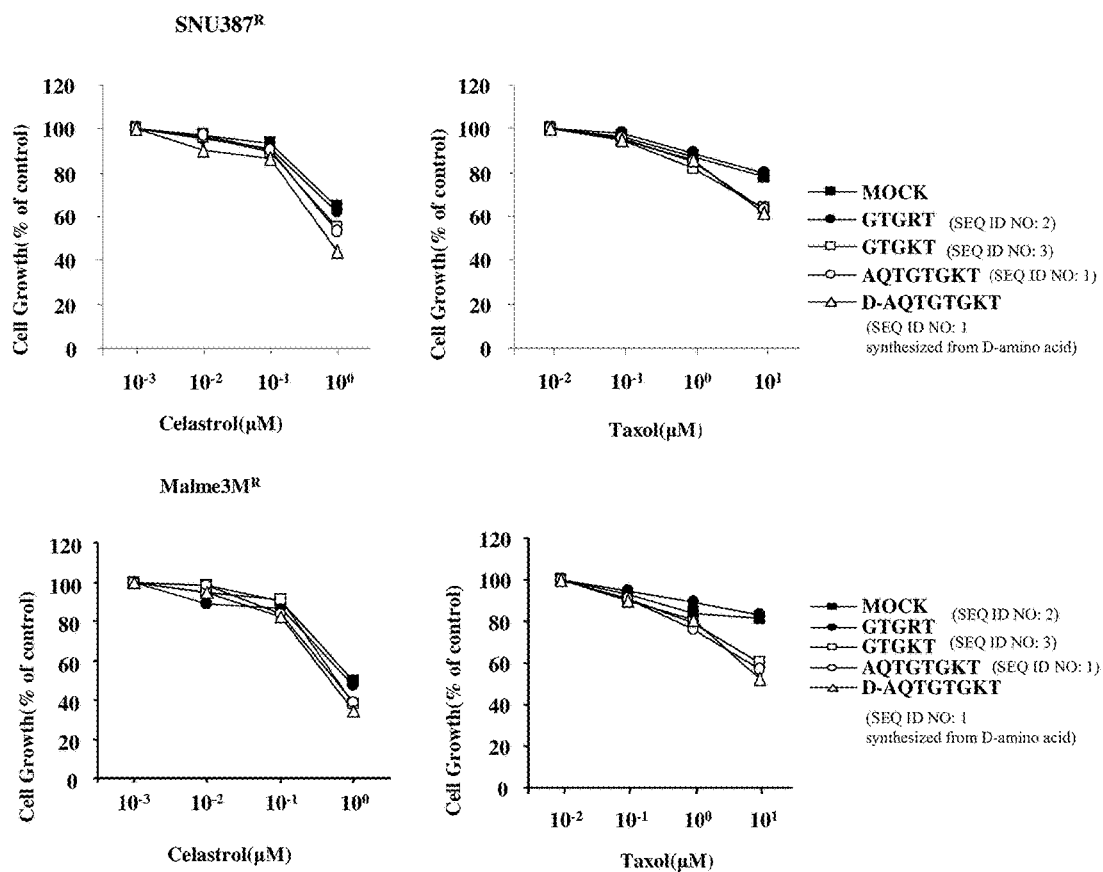

In addition, as a result of MTT assay shown in FIG. 1B, both two types of peptides inhibited the resistance to anticancer drugs in all the cancer cell lines.

Example 2: Examination on Intracellular Migration and Action of CAGE-Derived 8-Mer Peptides In order to examine the intercellular migration and action mechanisms of AQTGTGKT (SEQ ID NO: 1 synthesized from L-amino acid) and D-AQTGTGKT (SEQ ID NO: 1 synthesized from D-amino acid) peptides, each of the peptides was prepared in a form of being conjugated to fluorescein isothiocyanate (FITC), and used to perform transfection, immunofluorescence, immunoprecipitation, and western blotting by known methods.

Figure 2A:
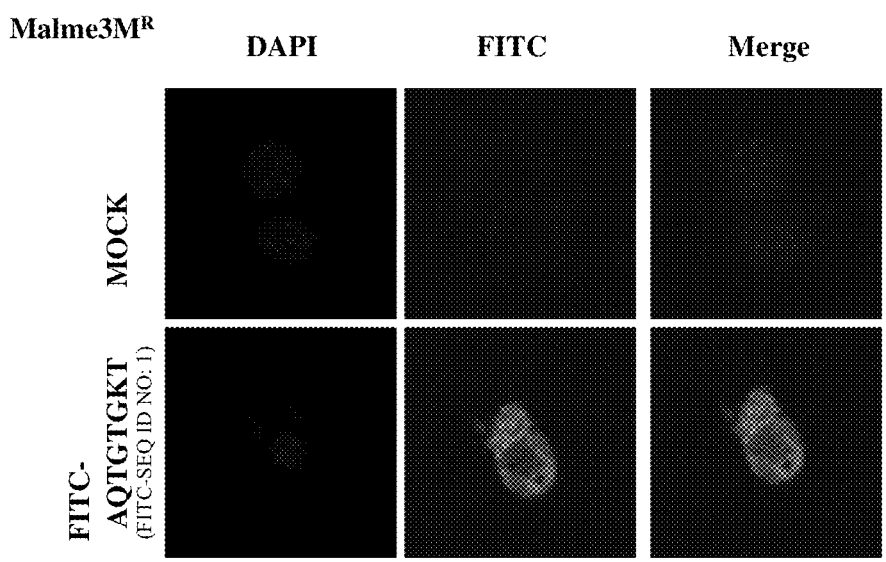
FIGS. 2A, 2B, and 2C illustrate the results showing that, when SNU387$^R$ or Malme3M$^R$ cell line was treated with a green fluorescence reagent (FITC, fluorescein isothiocyanate)-labeled AQTGTGKT peptide (FITC-SEQ ID NO: 1), the peptide migrated into the anticancer drug-resistant cells.

Celastrol-resistant liver cancer cell line (SNU387$^R$) and melanoma cell line (Malme3M$^R$) having high expression of CAGE were transfected with FITC-AQTGTGKT (FITC-SEQ ID NO: 1) peptide, and after 24 hours, the cell lines were examined under a fluorescent microscope. The results, as shown in FIG. 2A, confirmed that each peptide migrated into the cells.

Figure 2B:
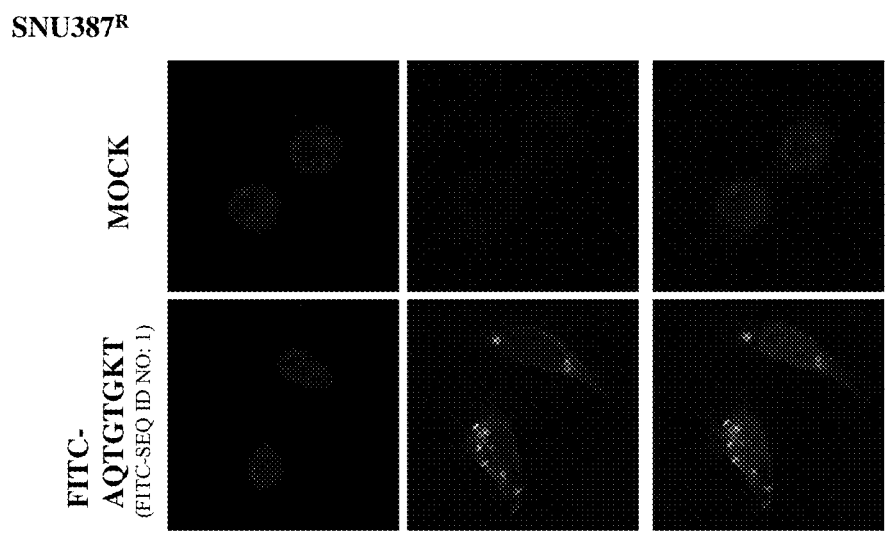

The same cell lines were transfected with AQTGTGKT (SEQ ID NO: 1 synthesized from L-amino acid) or FITC-AQTGTGKT (FITC-SEQ ID NO: 1) peptide, and then subjected to immunoprecipitation and western blotting. The results, as shown in FIG. 2B, showed that each peptide inhibited the dephosphorylation of GSK3β ser9 and the expression of Cyclin D1.

In addition, the cell lines were transfected with AQTGTGKT (SEQ ID NO: 1 synthesized from L-amino acid) or D-AQTGTGKT (SEQ ID NO: 1 synthesized from D-amino acid) peptide, and then subjected to immunoprecipitation and western blotting. The results, as shown in FIG. 3, showed that each peptide inhibited the dephosphorylation of GSK3β ser9 and the expression of Cyclin D1 and inhibited the interconnection of CAGE and GSK3β proteins.

Example 3: Examination on Effect of CAGE-Derived 8-Mer Peptide on Tumorigenicity of Anticancer Drug-Resistant Cell Line In order to examine that the AQTGTGKT (SEQ ID NO: 1 synthesized from L-amino acid) is a tumor-specific peptide, experiments were carried out by a known method using an anticancer drug-resistant cell line and an immune-deficient mouse.

Celastrol-resistant melanoma cell line (Malme3M$^R$) having high expression of CAGE was injected into the side of a nude mouse at $1 \times 10^6$ cells. When a tumor was grown to have a measurable tumor size, the tumor size was measured using a digital gauge at regular intervals, and the tumor size was calculated using a known formula (widest length× shortest length$^2 \times 0.5$).

Figure 4A:
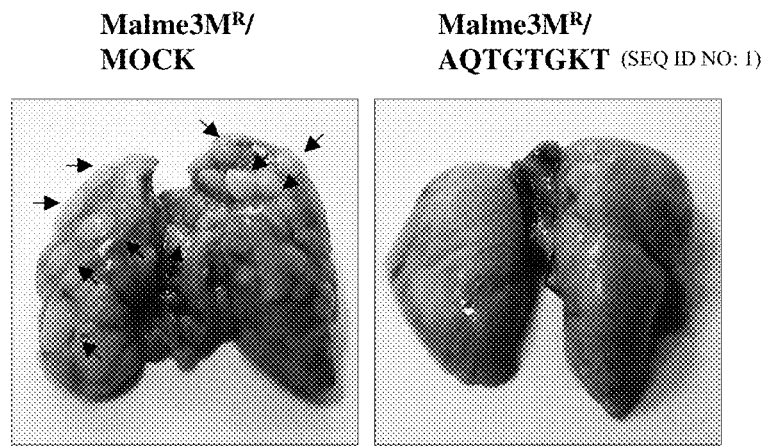
FIGS. 4A and 4B illustrate the results showing that SEQ ID NO: 1 synthesized from L-amino acid (AQTGTGKT) peptide reduced metastatic ability of Malme3M$^R$ cell line.

After the tumor was induced by the above method, AQTGTGKT (SEQ ID NO: 1 synthesized from L-amino acid) peptide (10 μg/mouse) was injected into the tail vein alone or in combination with Celastrol or Taxol anticancer drug in a total of 6 times every 3 days for 2 weeks, while the size of the tumor was measured. The results, as shown in FIG. 4A, showed that the AQTGTGKT (SEQ ID NO: 1 synthesized from L-amino acid) peptide reduced tumorigenicity and anticancer drug resistance.

Figure 4B:
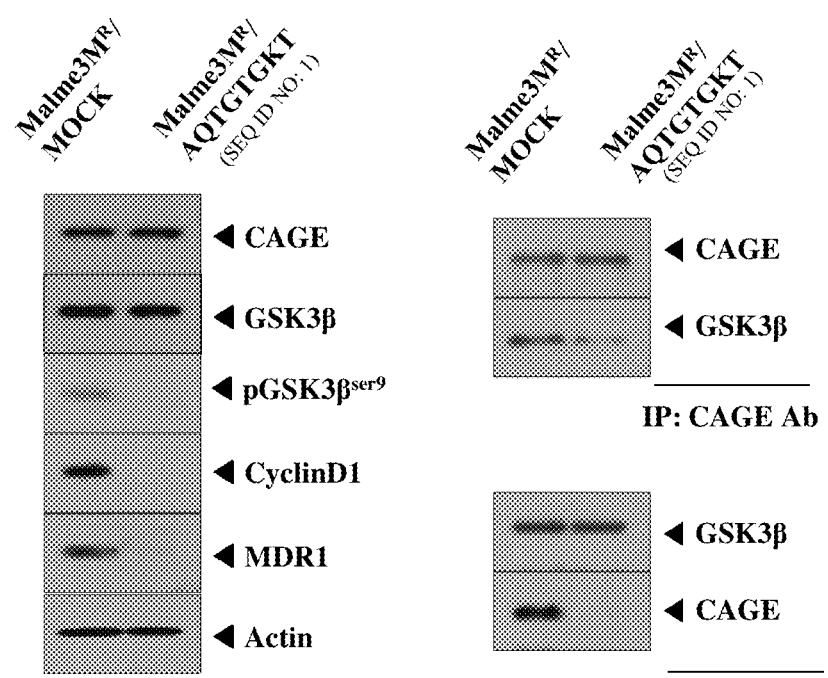

After the above experiments, the protein expression and activation were examined. The tumor tissues were disrupted by liquid nitrogen according to a known method, reacted with a dissolution buffer on ice for 30 minutes, and centrifuged at 13,000 rpm for 15 minutes, and then the supernatant solution was collected as a protein sample. Thereafter, this protein sample was subjected to western blotting and immunoprecipitation to examine the protein expression and activation and the interconnection of proteins. The results, as shown in FIG. 4B, showed that the AQTGTGKT (SEQ ID NO: 1 synthesized from L-amino acid) peptide inhibited the interconnection of CAGE and GSK3β proteins to induce the reductions in GSK3β ser9 dephosphorylation and cyclin D1 expression, and inhibited the expression of MDR1, which is an anticancer drug resistant gene.

Example 4: Examination on CAGE-Derived 8-Mer Peptide on Metastatic Ability of Anticancer Drug-Resistant Cell Line In order to examine the effect of AQTGTGKT (SEQ ID NO: 1 synthesized from L-amino acid) peptide on tumor metastatic ability of an anticancer drug-resistant cell line, long metastasis was carried out using the anticancer drug-resistant cell line and an immunodeficient mouse by a known method.

Celastrol-resistant melanoma cell line (Malme3M$^R$) having high expression of CAGE was injected into the tail vein of a nude mouse at $1 \times 10^6$ cells, and then the metastasis of a tumor into the lung was induced for 2-3 weeks. From day 4 after tumor cell injection, AQTGTGKT (SEQ ID NO: 1 synthesized from L-amino acid) peptide (10 μg/mouse) was injected into the tail vein in a total of 6 times every 3 days, and the lung tissue was excised and the number of tumor nodules was measured by a known method. The resultsshowhed that the AQTGTGKT (SEQ ID NO: 1 synthesized from L-amino acid) peptide reduced the tumor metastasis by the Celastrol-resistant melanoma cell line (Malme3M$^R$).

After the protein was collected from the lung tissues by a conventional method, the protein expression and activation patterns were examined through immunoprecipitation and western blotting. The resultsconfirmed that the AQTGTGKT peptide inhibited the dephosphorylation of GSK3β ser9 and the expression of Cyclin D1 and inhibited the interconnection of CAGE and GSK3β proteins.

Example 5: Examination on Effects of CAGE-Derived 8-Mer Peptides on Migration, Invasiveness, and Angiogenesis Inducing Ability of Anticancer Drug-Resistant Cell Line In order to examine the effects of AQTGTGKT (SEQ ID NO: 1 synthesized from L-amino acid) and D-AQTGTGKT (SEQ ID NO: 1 synthesized from D-amino acid) peptides on the migration, invasivenss, and angiogenesis inducing ability of anticancer drug-resistant cell line, the invasion assay, wound-healing migration assay, and intravital microscopy were carried out by conventional methods using Celastrol-resistant melanoma cell line (Malme3M$^R$).

Figure 2C:
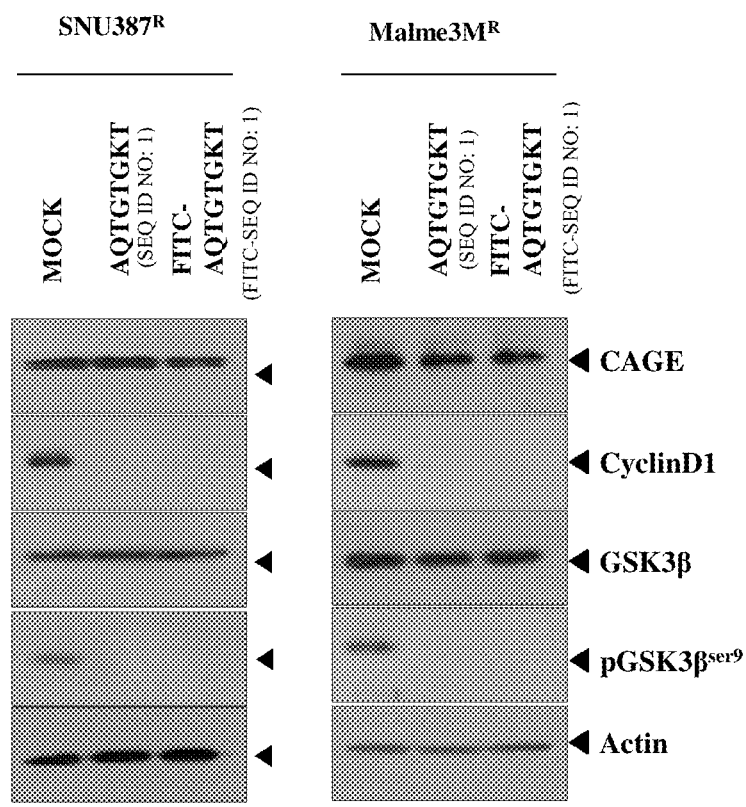
Figure 3A:
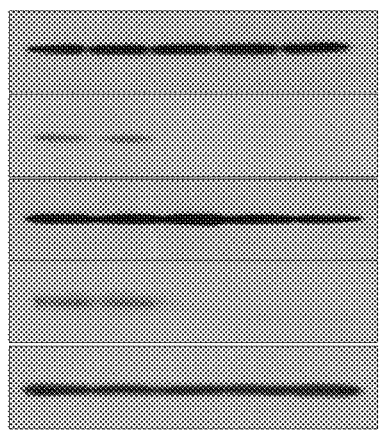
FIGS. 3A and 3B illustrate the results showing that SEQ ID NO: 1 synthesized from L-amino acid (AQTGTGKT) or SEQ ID NO: 1 synthesized from D-amino acid (D-AQTGTGKT) peptide inhibited the connection of CAGE and GSK3β in SNU387$^R$ or Malme3M$^R$ cell line.
Figure 3A:
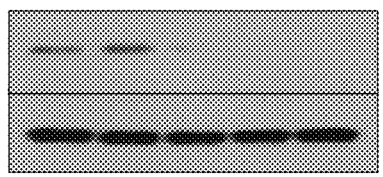
Figure 3A:
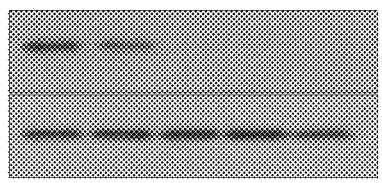
Figure 3B:
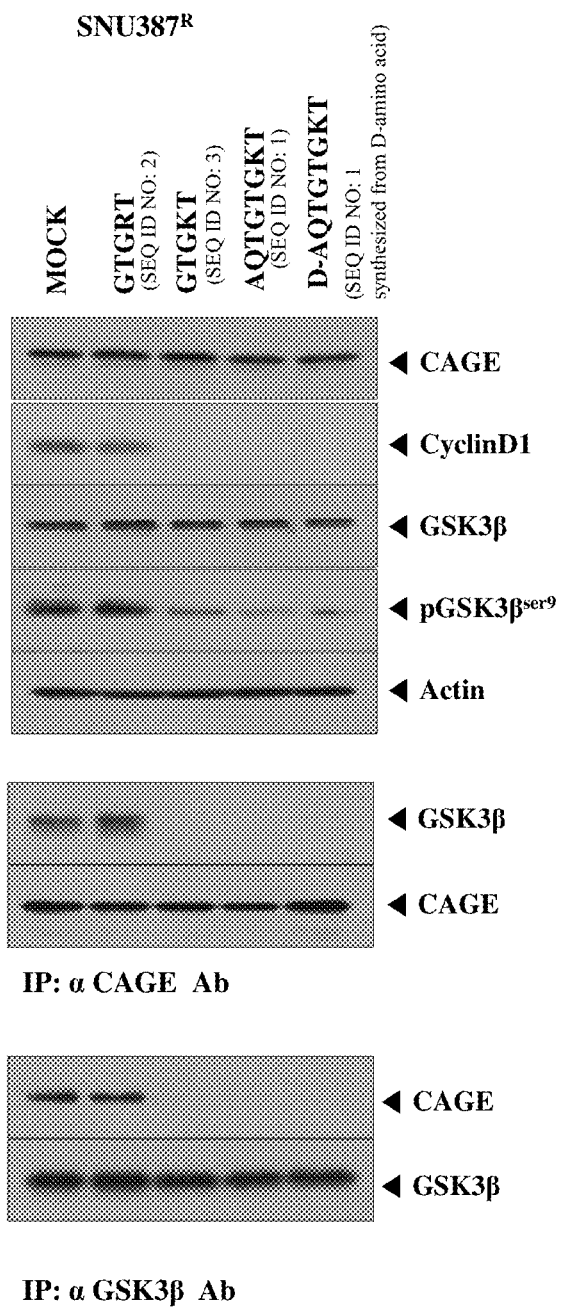

Celastrol-resistant melanoma cell line (Malme3MR) or Taxol-resistant melanoma cell line (Malme3M$^{R-Taxol}$) was cultured in 24-well culture dishes, and wounded using a 1 ml tip by a conventional method, and then the migrating cells were counted for 24-48 hours. The results, as shown in FIGS. 5A1 and 5A2, showed that AQTGTGKT (SEQ ID NO: 1 synthesized from L-amino acid) and D-AQTGTGKT (SEQ ID NO: 1 synthesized from D-amino acid) peptides inhibited cell migration.

Figure 5B:
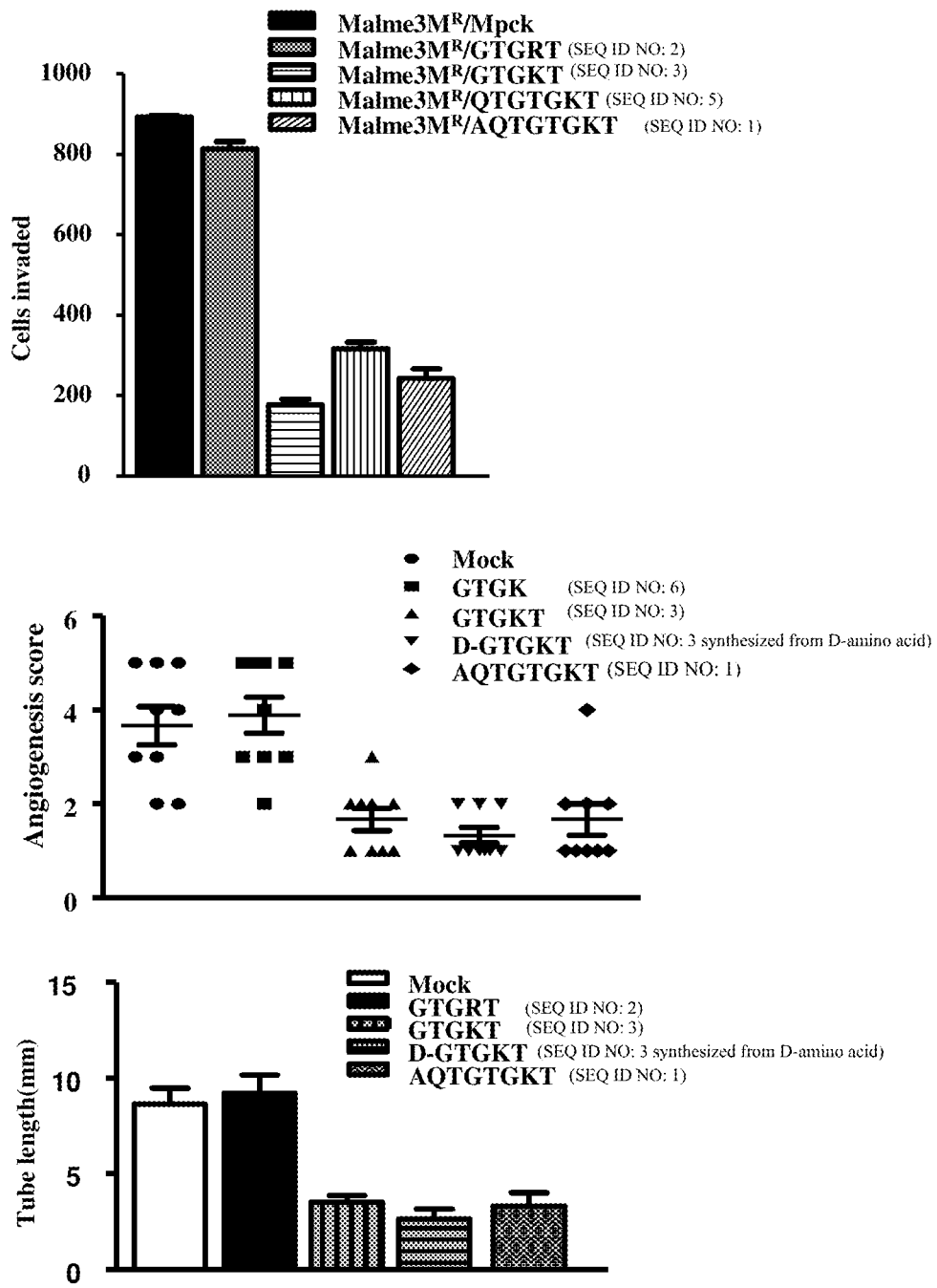
FIG. 5B illustrates the results showing that SEQ ID NO: 1 synthesized from L-amino acid (AQTGTGKT) peptide reduced the invasion ability of Malme3M$^R$ cell line.

After 5,000 Celastrol-resistant melanoma cell lines (Malme3M$^R$) were added together with serum-deficient media (FBS free media) in the upper chamber of transwell coated with 2 mg/ml matrigel, and cultured in growth media (10% FBS-media) for 24 hours, and then the invading cells were counted. The results, as shown in FIG. 5B, showed that the AQTGTGKT (SEQ ID NO: 1 synthesized from L-amino acid) and D-AQTGTGKT (SEQ ID NO: 1 synthesized from D-amino acid) peptides inhibited the invasiveness of anticancer drug resistant cell lines by about 50% or more.

Figure 5C:
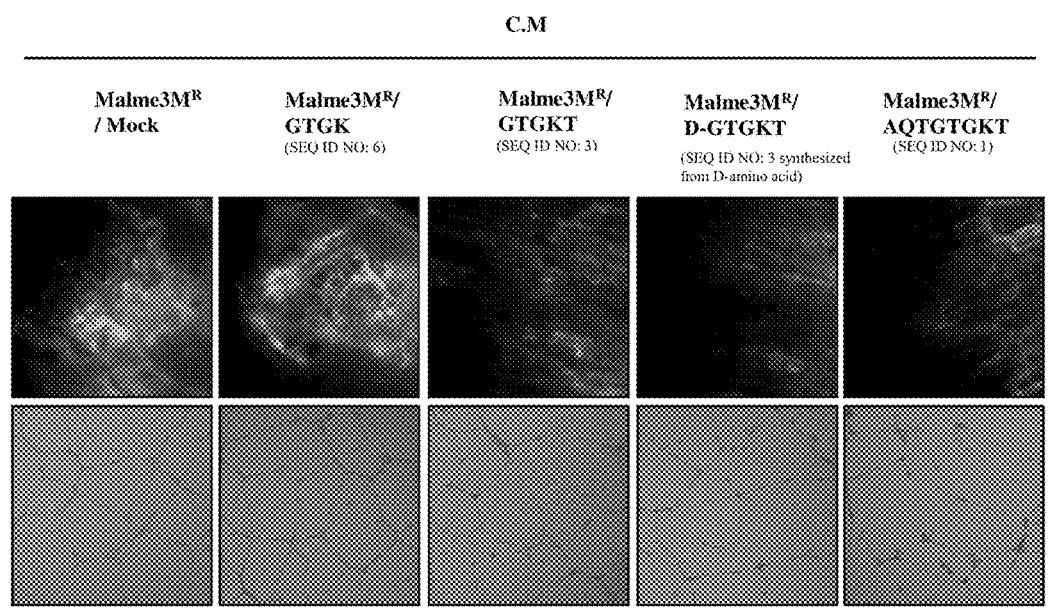
FIG. 5C illustrates the results showing that SEQ ID NO: 1 synthesized from L-amino acid (AQTGTGKT) peptide reduced the angiogenesis inducing ability of Malme3M$^R$ cell line.

After Celastrol-resistant melanoma cell line (Malme3M$^R$) was treated with AQTGTGKT (SEQ ID NO: 1 synthesized from L-amino acid) or D-AQTGTGKT (SEQ ID NO: 1 synthesized from D-amino acid) peptide, the obtained conditioned media were mixed with Matrigel and then injected into BALB/C mice, and then the mice were injected with FITC-dextran to examine the effect on angiogenesis using intravital microscopy. The results, as shown in FIG. 5C, showed that AQTGTGKT (SEQ ID NO: 1 synthesized from L-amino acid) and D-AQTGTGKT (SEQ ID NO: 1 synthesized from D-amino acid) peptides remarkably reduced angiogenesis inducing ability of Celastrol-resistant melanoma cell line (Malme3M$^R$).

Example 6: Examination on Tumor-Specific Migration of CAGE-Derived 8-Mer Peptide In order to examine that the AQTGTGKT (SEQ ID NO: 1 synthesized from L-amino acid) peptide is a tumor-specific peptide, experiments were carried out by a known method using FITC-AQTGTGKT (FITC-SEQ ID NO: 1) and anticancer drug-resistant cell lines and immunodeficient mice.

Figure 6:
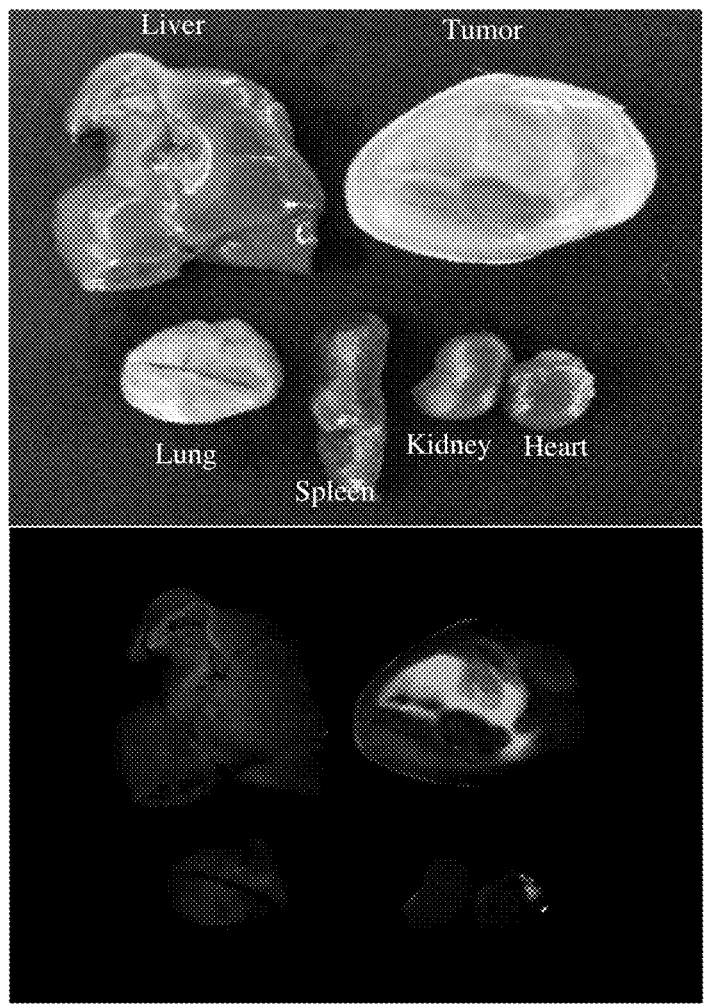
FIG. 6 shows tumor invasion ability (in vivo homing) results of SEQ ID NO: 1 synthesized from L-amino acid (AQTGTGKT) peptide, indicating that FITC-SEQ ID NO: 1 peptide migrated in a tumor tissue-specific manner.

Celastrol-resistant melanoma cell line (Malme3M$^R$) having high expression of CAGE was injected into immunodeficient mice by a known method to induce tumors, and then 12 hours after FITC-AQTGTGKT (FITC-SEQ ID NO: 1) was injected into the tail vein, normal tissues (brain, heart, spleen, Liver, lung, etc.) and tumor tissues were extracted and examined using a small in vivo imaging system. The results, as shown in FIG. 6, showed that FITC-AQTGTGKT (FITC-SEQ ID NO: 1) migrated specifically to tumor tissues.

The pharmaceutical composition of the present invention can effectively reduce anticancer drug resistance of cancer cells or cancer tissues having anticancer drug resistance, thereby increasing the therapeutic effect using anticancer drugs, and the pharmaceutical composition per se retains excellent anticancer activity, and thus can be used as a new anticancer drug.

The oligopeptide, which is an active ingredient of the pharmaceutical composition of the present invention, has a small molecular weight, unlike antibodies, and thus have few concerns of immune responses and are easy to invade tissues, and the oligopeptide can selectively act on cancer cells or cancer tissues, and thus can effectively solve side effects of an existing anticancer drug.

Sequence Listing Free Text
AQTGTGKT

EFFECTS OF THE INVENTION

The pharmaceutical composition of the present invention can effectively reduce anticancer drug resistance of cancer cells or cancer tissues having anticancer drug resistance, thereby increasing the therapeutic effect using anticancer drugs, and the pharmaceutical composition per se retains excellent anticancer activity, and thus can be used as a new anticancer drug.

The oligopeptide, which is an active ingredient of the pharmaceutical composition of the present invention, has a small molecular weight, unlike antibodies, and thus have few concerns of immune responses and are easy to invade tissues, and the oligopeptide can selectively act on cancer cells or cancer tissues, and thus can effectively solve side effects of an existing anticancer drug.

What is claimed is:

1. A method for increasing activity of an anticancer drug in a patient comprising:
    administering to a patient in need thereof an isolated peptide consisting of the amino acid sequence of SEQ ID NO: 1 (AQTGTGKT).

2. The method of claim 1, wherein the peptide is synthesized from L-amino acid or D-amino acid.

3. The method of claim 1, wherein the peptide consisting of the amino acid sequence of SEQ ID NO: 1 (AQTGTGKT) increases the anticancer activity by reducing anticancer drug resistance of cancer cells or cancer tissues.

4. The method of claim 1, wherein the anticancer drug is Celastrol or Taxol.

5. The method of claim 1, wherein the patient in need is a cancer patient.

6. The method of claim 5, wherein the cancer is liver cancer or melanoma.

7. The method of claim 5, wherein the cancer has tumor tissue having a high CAGE expression.

8. The method of claim 5, wherein the cancer is caused by cancer cells having resistance to Celastrol or Taxol.

9. A method for treating a cancer in a patient in need thereof comprising: administering an isolated peptide consisting of the amino acid sequence of SEQ ID NO: 1 (AQTGTGKT), wherein the cancer is selected from the group consisting of liver cancer or melanoma, cancer has tumor tissue having a high CAGE expression, and the cancer is caused by cancer cells having resistance to Celastrol or Taxol.

* * * * *